US009861294B2

(12) United States Patent
Jones et al.

(10) Patent No.: US 9,861,294 B2
(45) Date of Patent: Jan. 9, 2018

(54) MARKER DELIVERY DEVICE WITH RELEASABLE PLUG

(71) Applicant: SenoRx, Inc., Tempe, AZ (US)

(72) Inventors: Michael L. Jones, San Clemente, CA (US); Paul Lubock, Monarch Beach, CA (US); John Merritt, San Clemente, CA (US)

(73) Assignee: SenoRx, Inc., Tempe, AZ (US)

( * ) Notice: Subject to any disclaimer, the term of this patent is extended or adjusted under 35 U.S.C. 154(b) by 309 days.

(21) Appl. No.: 14/608,939

(22) Filed: Jan. 29, 2015

(65) Prior Publication Data

US 2015/0141805 A1    May 21, 2015

Related U.S. Application Data

(63) Continuation of application No. 13/750,341, filed on Jan. 25, 2013, now Pat. No. 9,044,162, which is a
(Continued)

(51) Int. Cl.
*A61B 19/00* (2006.01)
*A61B 5/06* (2006.01)
*A61B 17/00* (2006.01)
*A61M 37/00* (2006.01)
*A61B 5/055* (2006.01)
*A61B 6/12* (2006.01)
*A61B 8/08* (2006.01)
*A61B 10/02* (2006.01)
(Continued)

(52) U.S. Cl.
CPC .............. *A61B 5/064* (2013.01); *A61B 5/055* (2013.01); *A61B 5/062* (2013.01); *A61B 6/12* (2013.01);
(Continued)

(58) Field of Classification Search
CPC ............ A61B 19/54; A61B 2019/5404; A61B 2019/5408; A61B 2019/5412;
(Continued)

(56) References Cited

U.S. PATENT DOCUMENTS 2,481,408 A    9/1949 Fuller et al.
2,899,362 A    8/1959 Sieger, Jr. et al.
(Continued)

FOREIGN PATENT DOCUMENTS

| DE | 1029528 B | 5/1958 |
|---|---|---|
| EP | 0146699 A1 | 7/1985 |
| EP | 0255123 A2 | 2/1988 |
| EP | 0292936 A2 | 11/1988 |
| EP | 0458745 A1 | 11/1991 |
| EP | 0475077 A2 | 3/1992 |
| EP | 0552924 A1 | 7/1993 |
| EP | 0769281 A2 | 4/1997 |

(Continued)

OTHER PUBLICATIONS

Fajardo, Laurie, et al., "Placement of Endovascular Embolization Microcoils to Localize the Site of Breast Lesions Removed at Stereotactic Core Biopsy", Radiology, Jan. 1998, pp. 275-278, vol. 206—No. 1
(Continued)

*Primary Examiner* — Tuan V Nguyen

(57) ABSTRACT

A marker delivery device includes an elongated delivery cannula which has a distal end section, an inner lumen and a discharge opening in the distal end section in communication with the inner lumen. A plunger is slidably disposed within the inner lumen of the elongated delivery cannula. The plunger has a distal end. At least one elongated fibrous marker body is pre-formed prior to being inserted into the inner lumen of the elongated delivery cannula. The at least one elongated fibrous marker body is slidably disposed within the inner lumen of the elongated delivery cannula at a location distal to the distal end of the plunger. The pre-formed at least one elongated fibrous marker body includes a fibrous material compressed and impregnated with a binding agent and freeze dried in the compressed condition. A releasable plug is disposed within a distal portion of the inner lumen and distal to the at least one elongated fibrous marker body.

20 Claims, 5 Drawing Sheets

Related U.S. Application Data continuation of application No. 13/037,971, filed on Mar. 1, 2011, now Pat. No. 8,361,082, which is a continuation-in-part of application No. 10/753,694, filed on Jan. 7, 2004, now abandoned, which is a continuation-in-part of application No. 10/444,770, filed on May 23, 2003, now Pat. No. 7,983,734, said application No. 13/037,971 is a continuation-in-part of application No. 12/852,286, filed on Aug. 6, 2010, now Pat. No. 8,219,182, which is a continuation of application No. 10/990,327, filed on Nov. 16, 2004, now Pat. No. 7,792,569, which is a continuation of application No. 10/124,757, filed on Apr. 16, 2002, now Pat. No. 6,862,470, which is a continuation-in-part of application No. 09/717,909, filed on Nov. 20, 2000, now Pat. No. 6,725,083, which is a continuation-in-part of application No. 09/343,975, filed on Jun. 30, 1999, now Pat. No. 6,347,241, which is a continuation-in-part of application No. 09/241,936, filed on Feb. 2, 1999, now Pat. No. 6,161,034, said application No. 13/037,971 is a continuation-in-part of application No. 12/592,020, filed on Nov. 18, 2009, now Pat. No. 8,177,792, which is a continuation of application No. 10/174,401, filed on Jun. 17, 2002, now Pat. No. 7,651,505.

(51) Int. Cl.
  *A61M 5/00*      (2006.01)
  *A61K 49/12*     (2006.01)
  *A61K 49/18*     (2006.01)
  *A61B 90/00*     (2016.01)

(52) U.S. Cl.
  CPC ............ *A61B 8/0833* (2013.01); *A61B 10/02* (2013.01); *A61B 17/0057* (2013.01); *A61B 90/39* (2016.02); *A61K 49/12* (2013.01); *A61K 49/18* (2013.01); *A61M 5/007* (2013.01); *A61M 37/0069* (2013.01); *A61B 2017/00637* (2013.01); *A61B 2017/00898* (2013.01); *A61B 2090/3908* (2016.02); *A61B 2090/3925* (2016.02); *A61B 2090/3954* (2016.02); *A61B 2090/3966* (2016.02); *A61B 2090/3987* (2016.02); *A61K 2123/00* (2013.01)

(58) Field of Classification Search
  CPC . A61B 2019/5416; A61B 5/064; A61B 5/055; A61B 5/062; A61B 5/12; A61B 8/0833; A61B 10/02; A61B 17/0057; A61K 49/12; A61K 49/18
  See application file for complete search history.

(56) References Cited

U.S. PATENT DOCUMENTS

| | | |
|---|---|---|
| 2,907,327 A | 10/1959 | White |
| 3,005,457 A | 10/1961 | Millman |
| 3,128,744 A | 4/1964 | Jefferts et al. |
| 3,341,417 A | 9/1967 | Sinaiko |
| 3,402,712 A | 9/1968 | Eisenhand |
| 3,516,412 A | 6/1970 | Ackerman |
| 3,593,343 A | 7/1971 | Viggers |
| 3,757,781 A | 9/1973 | Smart |
| 3,818,894 A | 6/1974 | Wichterle et al. |
| 3,820,545 A | 6/1974 | Jefferts |
| 3,823,212 A | 7/1974 | Chvapil |
| 3,892,731 A | 7/1975 | Austin |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,086,914 A | 5/1978 | Moore |
| 4,103,690 A | 8/1978 | Harris |
| 4,105,030 A | 8/1978 | Kercso |
| 4,127,774 A | 11/1978 | Gillen |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,347,234 A | 8/1982 | Wahlig et al. |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,718,433 A | 1/1988 | Feinstein |
| 4,740,208 A | 4/1988 | Cavon |
| 4,762,128 A | 8/1988 | Rosenbluth |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A | 7/1990 | Dunn et al. |
| 4,950,234 A | 8/1990 | Fujioka et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,013 A | 2/1991 | Suthanthiran et al. |
| 4,994,028 A | 2/1991 | Leonard et al. |
| 5,012,818 A | 5/1991 | Joishy |
| 5,013,090 A | 5/1991 | Matsuura |
| 5,018,530 A | 5/1991 | Rank et al. |
| 5,035,891 A | 7/1991 | Runkel et al. |
| 5,059,197 A | 10/1991 | Urie et al. |
| 5,081,997 A | 1/1992 | Bosley, Jr. et al. |
| 5,108,421 A * | 4/1992 | Fowler ............... A61B 17/0057 604/15 |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,295 A | 9/1992 | Stewart |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,482 A | 3/1993 | Rank et al. |
| 5,197,846 A | 3/1993 | Uno et al. |
| 5,199,441 A | 4/1993 | Hogle |
| 5,201,704 A | 4/1993 | Ray |
| 5,219,339 A | 6/1993 | Saito |
| 5,221,269 A | 6/1993 | Miller et al. |
| 5,231,615 A | 7/1993 | Endoh |

(56) References Cited

U.S. PATENT DOCUMENTS

| | | |
|---|---|---|
| 5,234,426 A | 8/1993 | Rank et al. |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,312,435 A | 5/1994 | Nash et al. |
| 5,320,100 A | 6/1994 | Herweck et al. |
| 5,320,613 A | 6/1994 | Houge et al. |
| 5,328,955 A | 7/1994 | Rhee et al. |
| 5,334,216 A | 8/1994 | Vidal et al. |
| 5,334,381 A | 8/1994 | Unger |
| 5,344,640 A | 9/1994 | Deutsch et al. |
| 5,353,804 A | 10/1994 | Kornberg et al. |
| 5,354,623 A | 10/1994 | Hall |
| 5,358,514 A | 10/1994 | Schulman et al. |
| 5,360,416 A | 11/1994 | Ausherman et al. |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,405,402 A | 4/1995 | Dye et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A | 7/1995 | Shaw |
| 5,433,204 A | 7/1995 | Olson |
| 5,444,113 A | 8/1995 | Sinclair et al. |
| 5,449,560 A | 9/1995 | Antheunis et al. |
| 5,451,406 A | 9/1995 | Lawin et al. |
| 5,458,643 A | 10/1995 | Oka et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,545,180 A | 8/1996 | Le et al. |
| 5,549,560 A | 8/1996 | Van de Wijdeven |
| 5,567,413 A | 10/1996 | Klaveness et al. |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,657,366 A | 8/1997 | Nakayama |
| 5,665,092 A | 9/1997 | Mangiardi et al. |
| 5,667,767 A | 9/1997 | Greff et al. |
| 5,669,882 A | 9/1997 | Pyles |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,682 A | 12/1997 | Thompson |
| 5,702,716 A | 12/1997 | Dunn et al. |
| 5,716,981 A | 2/1998 | Hunter et al. |
| 5,747,060 A | 5/1998 | Sackler et al. |
| 5,752,974 A | 5/1998 | Rhee et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,771 A | 7/1998 | Hussman |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,808,007 A | 9/1998 | Lee et al. |
| 5,810,884 A * | 9/1998 | Kim ............... A61B 17/0057 606/213 |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,826,776 A | 10/1998 | Schulze et al. |
| 5,830,178 A | 11/1998 | Jones et al. |
| 5,830,222 A | 11/1998 | Makower |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,461 A | 12/1998 | Bakis et al. |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,916,164 A | 6/1999 | Fitzpatrick et al. |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,439 A | 8/1999 | Kammerer et al. |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,976,146 A | 11/1999 | Ogawa et al. |
| 5,980,564 A | 11/1999 | Stinson |
| 5,989,265 A | 11/1999 | Bouquet De La Joliniere et al. |
| 6,015,541 A | 1/2000 | Greff et al. |
| 6,027,471 A | 2/2000 | Fallon et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,090,996 A | 7/2000 | Li |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,135,993 A | 10/2000 | Hussman |
| 6,142,955 A | 11/2000 | Farascioni et al. |
| 6,159,240 A | 12/2000 | Sparer et al. |

(56) References Cited

U.S. PATENT DOCUMENTS

| | | |
|---|---|---|
| 6,159,445 A | 12/2000 | Klaveness et al. |
| 6,162,192 A | 12/2000 | Cragg et al. |
| 6,166,079 A | 12/2000 | Follen et al. |
| 6,173,715 B1 | 1/2001 | Sinanan et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,190,353 B1 | 2/2001 | Makower et al. |
| 6,200,258 B1 | 3/2001 | Slater et al. |
| 6,203,507 B1 | 3/2001 | Wadsworth et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,135 B1 | 6/2001 | Stinson et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,306,154 B1 | 10/2001 | Hudson et al. |
| 6,312,429 B1 | 11/2001 | Burbank et al. |
| 6,316,522 B1 | 11/2001 | Loomis et al. |
| 6,325,789 B1 | 12/2001 | Janzen et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 | 4/2002 | Sirimanne et al. |
| 6,394,965 B1 | 5/2002 | Klein |
| 6,403,758 B1 | 6/2002 | Loomis |
| 6,405,733 B1 | 6/2002 | Fogarty et al. |
| 6,409,742 B1 | 6/2002 | Fulton, III et al. |
| 6,419,621 B1 | 7/2002 | Sioshansi et al. |
| 6,424,857 B1 | 7/2002 | Henrichs et al. |
| 6,425,903 B1 | 7/2002 | Voegele |
| 6,427,081 B1 | 7/2002 | Burbank et al. |
| 6,436,030 B2 | 8/2002 | Rehil |
| 6,447,524 B1 | 9/2002 | Knodel et al. |
| 6,447,527 B1 | 9/2002 | Thompson et al. |
| 6,450,937 B1 | 9/2002 | Mercereau et al. |
| 6,450,938 B1 | 9/2002 | Miller |
| 6,471,700 B1 | 10/2002 | Burbank et al. |
| 6,478,790 B2 | 11/2002 | Bardani |
| 6,506,156 B1 | 1/2003 | Jones et al. |
| 6,511,468 B1 | 1/2003 | Cragg et al. |
| 6,511,650 B1 | 1/2003 | Eiselt et al. |
| 6,537,193 B1 | 3/2003 | Lennox |
| 6,540,981 B2 | 4/2003 | Klaveness et al. |
| 6,544,185 B2 | 4/2003 | Montegrande |
| 6,544,231 B1 | 4/2003 | Palmer et al. |
| 6,551,253 B2 | 4/2003 | Worm et al. |
| 6,554,760 B2 | 4/2003 | Lamoureux et al. |
| 6,562,317 B2 | 5/2003 | Greff et al. |
| 6,564,806 B1 | 5/2003 | Fogarty et al. |
| 6,565,551 B1 | 5/2003 | Jones et al. |
| 6,567,689 B2 | 5/2003 | Burbank et al. |
| 6,575,888 B2 | 6/2003 | Zamora et al. |
| 6,575,991 B1 | 6/2003 | Chesbrough et al. |
| 6,585,773 B1 | 7/2003 | Xie |
| 6,605,047 B2 | 8/2003 | Zarins et al. |
| 6,610,026 B2 | 8/2003 | Cragg et al. |
| 6,613,002 B1 | 9/2003 | Clark et al. |
| 6,616,630 B1 | 9/2003 | Woehr et al. |
| 6,626,850 B1 | 9/2003 | Chau et al. |
| 6,626,899 B2 | 9/2003 | Houser et al. |
| 6,628,982 B1 | 9/2003 | Thomas et al. |
| 6,629,947 B1 | 10/2003 | Sahatjian et al. |
| 6,636,758 B2 | 10/2003 | Sanchez et al. |
| 6,638,234 B2 | 10/2003 | Burbank et al. |
| 6,638,308 B2 | 10/2003 | Corbitt, Jr. et al. |
| 6,652,442 B2 | 11/2003 | Gatto |
| 6,656,192 B2 | 12/2003 | Espositio et al. |
| 6,659,933 B2 | 12/2003 | Asano |
| 6,662,041 B2 | 12/2003 | Burbank et al. |
| 6,699,205 B2 | 3/2004 | Fulton, III et al. |
| 6,712,774 B2 | 3/2004 | Voegele et al. |
| 6,712,836 B1 | 3/2004 | Berg et al. |
| 6,716,444 B1 | 4/2004 | Castro et al. |
| 6,730,042 B2 | 5/2004 | Fulton et al. |
| 6,730,044 B2 | 5/2004 | Stephens et al. |
| 6,746,661 B2 | 6/2004 | Kaplan |
| 6,746,773 B2 | 6/2004 | Llanos et al. |
| 6,752,154 B2 | 6/2004 | Fogarty et al. |
| 6,766,186 B1 | 7/2004 | Hoyns et al. |
| 6,774,278 B1 | 8/2004 | Ragheb et al. |
| 6,780,179 B2 | 8/2004 | Lee et al. |
| 6,824,507 B2 | 11/2004 | Miller |
| 6,824,527 B2 | 11/2004 | Gollobin |
| 6,846,320 B2 | 1/2005 | Ashby et al. |
| 6,863,685 B2 | 3/2005 | Davila et al. |
| 6,881,226 B2 | 4/2005 | Corbitt, Jr. et al. |
| 6,889,833 B2 | 5/2005 | Seiler et al. |
| 6,899,731 B2 | 5/2005 | Li et al. |
| 6,918,927 B2 | 7/2005 | Bates et al. |
| 6,936,014 B2 | 8/2005 | Vetter et al. |
| 6,939,318 B2 | 9/2005 | Stenzel |
| 6,945,973 B2 | 9/2005 | Bray |
| 6,951,564 B2 | 10/2005 | Espositio et al. |
| 6,958,044 B2 | 10/2005 | Burbank et al. |
| 6,992,233 B2 | 1/2006 | Drake et al. |
| 6,993,375 B2 | 1/2006 | Burbank et al. |
| 6,994,712 B1 | 2/2006 | Fisher et al. |
| 6,996,433 B2 | 2/2006 | Burbank et al. |
| 7,001,341 B2 | 2/2006 | Gellman et al. |
| 7,008,382 B2 | 3/2006 | Adams et al. |
| 7,014,610 B2 | 3/2006 | Koulik |
| 7,025,765 B2 | 4/2006 | Balbierz et al. |
| 7,041,047 B2 | 5/2006 | Gellman et al. |
| 7,044,957 B2 | 5/2006 | Foerster et al. |
| 7,047,063 B2 | 5/2006 | Burbank et al. |
| 7,083,576 B2 | 8/2006 | Zarins et al. |
| 7,125,397 B2 | 10/2006 | Woehr et al. |
| 7,135,978 B2 | 11/2006 | Gisselberg et al. |
| 7,160,258 B2 | 1/2007 | Imran et al. |
| 7,172,549 B2 | 2/2007 | Slater et al. |
| 7,189,206 B2 | 3/2007 | Quick et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |
| 7,280,865 B2 | 10/2007 | Adler |
| 7,294,118 B2 | 11/2007 | Saulenas et al. |
| 7,297,725 B2 | 11/2007 | Winterton et al. |
| 7,329,402 B2 | 2/2008 | Unger et al. |
| 7,329,414 B2 | 2/2008 | Fisher et al. |
| 7,407,054 B2 | 8/2008 | Seiler et al. |
| 7,416,533 B2 | 8/2008 | Gellman et al. |
| 7,424,320 B2 | 9/2008 | Chesbrough et al. |
| 7,449,000 B2 | 11/2008 | Adams et al. |
| 7,527,610 B2 | 5/2009 | Erickson |

(56) References Cited

U.S. PATENT DOCUMENTS

| | | |
|---|---|---|
| 7,534,452 B2 | 5/2009 | Chernomorsky et al. |
| 7,535,363 B2 | 5/2009 | Gisselberg et al. |
| 7,565,191 B2 | 7/2009 | Burbank et al. |
| 7,569,065 B2 | 8/2009 | Chesbrough et al. |
| 7,577,473 B2 | 8/2009 | Davis et al. |
| 7,637,948 B2 | 12/2009 | Corbitt, Jr. |
| 7,668,582 B2 | 2/2010 | Sirimanne et al. |
| 7,670,350 B2 | 3/2010 | Selis |
| 7,671,100 B2 | 3/2010 | Gaserod et al. |
| 7,783,336 B2 | 8/2010 | Macfarlane et al. |
| 7,819,819 B2 | 10/2010 | Quick et al. |
| 7,819,820 B2 | 10/2010 | Field et al. |
| 7,844,319 B2 | 11/2010 | Susil et al. |
| 7,877,133 B2 | 1/2011 | Burbank et al. |
| 7,914,553 B2 | 3/2011 | Ferree |
| 7,945,307 B2 | 5/2011 | Lubock et al. |
| 7,978,825 B2 | 7/2011 | Ngo |
| 8,011,508 B2 | 9/2011 | Seiler et al. |
| 8,027,712 B2 | 9/2011 | Sioshansi et al. |
| 8,052,658 B2 | 11/2011 | Field |
| 8,052,708 B2 | 11/2011 | Chesbrough et al. |
| 8,064,987 B2 | 11/2011 | Carr, Jr. |
| 8,128,641 B2 | 3/2012 | Wardle |
| 8,157,862 B2 | 4/2012 | Corbitt, Jr. |
| 8,306,602 B2 | 11/2012 | Sirimanne et al. |
| 8,311,610 B2 | 11/2012 | Ranpura |
| 8,320,993 B2 | 11/2012 | Sirimanne et al. |
| 8,320,994 B2 | 11/2012 | Sirimanne et al. |
| 8,320,995 B2 | 11/2012 | Schwamb, Jr. |
| 8,334,424 B2 | 12/2012 | Szypka |
| 8,401,622 B2 | 3/2013 | Talpade et al. |
| 8,414,602 B2 | 4/2013 | Selia |
| 8,437,834 B2 | 5/2013 | Carr, Jr. |
| 8,442,623 B2 | 5/2013 | Nicoson et al. |
| 8,454,629 B2 | 6/2013 | Selis |
| 8,486,028 B2 | 7/2013 | Field |
| 8,579,931 B2 | 11/2013 | Chesbrough et al. |
| 8,626,269 B2 | 1/2014 | Jones et al. |
| 8,626,270 B2 | 1/2014 | Burbank et al. |
| 8,639,315 B2 | 1/2014 | Burbank et al. |
| 8,668,737 B2 | 3/2014 | Corbitt, Jr. |
| 8,670,818 B2 | 3/2014 | Ranpura et al. |
| 8,680,498 B2 | 3/2014 | Corbitt et al. |
| 8,718,745 B2 | 5/2014 | Burbank et al. |
| 8,784,433 B2 | 7/2014 | Lubock et al. |
| 9,028,872 B2 | 5/2015 | Gaserod et al. |
| 9,044,162 B2 * | 6/2015 | Jones ................ A61B 17/0057 |
| 9,237,937 B2 | 1/2016 | Burbank et al. |
| 2001/0006616 A1 | 7/2001 | Leavitt et al. |
| 2001/0033867 A1 | 10/2001 | Ahern et al. |
| 2001/0049481 A1 | 12/2001 | Fulton, III et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0044969 A1 | 4/2002 | Harden et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082517 A1 | 6/2002 | Klein |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0177776 A1 | 11/2002 | Crawford Kellar et al. |
| 2002/0188195 A1 | 12/2002 | Mills |
| 2002/0193815 A1 | 12/2002 | Foerster et al. |
| 2002/0193867 A1 | 12/2002 | Gladdish, Jr. et al. |
| 2003/0032969 A1 | 2/2003 | Gannoe et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0030262 A1 | 2/2004 | Fisher et al. |
| 2004/0059341 A1 | 3/2004 | Gellman et al. |
| 2004/0068312 A1 | 4/2004 | Sigg et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0133124 A1 | 7/2004 | Bates et al. |
| 2004/0153074 A1 | 8/2004 | Bojarski et al. |
| 2004/0162574 A1 | 8/2004 | Viola |
| 2004/0167619 A1 | 8/2004 | Case et al. |
| 2004/0193044 A1 | 9/2004 | Burbank et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236211 A1 | 11/2004 | Burbank et al. |
| 2004/0236212 A1 | 11/2004 | Jones et al. |
| 2004/0253185 A1 | 12/2004 | Herweck et al. |
| 2004/0265371 A1 | 12/2004 | Looney et al. |
| 2005/0019262 A1 | 1/2005 | Chernomorsky et al. |
| 2005/0020916 A1 | 1/2005 | MacFarlane et al. |
| 2005/0033157 A1 | 2/2005 | Klien et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0063908 A1 | 3/2005 | Burbank et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0112151 A1 | 5/2005 | Horng |
| 2005/0113659 A1 | 5/2005 | Pothier et al. |
| 2005/0119562 A1 | 6/2005 | Jones et al. |
| 2005/0142161 A1 | 6/2005 | Freeman et al. |
| 2005/0143650 A1 | 6/2005 | Winkel |
| 2005/0143656 A1 | 6/2005 | Burbank et al. |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0216018 A1 | 9/2005 | Sennett |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0025677 A1 | 2/2006 | Verard et al. |
| 2006/0025795 A1 | 2/2006 | Chesbrough et al. |
| 2006/0036158 A1 | 2/2006 | Field et al. |
| 2006/0036159 A1 | 2/2006 | Sirimanne et al. |
| 2006/0036165 A1 | 2/2006 | Burbank et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |

(56) References Cited

U.S. PATENT DOCUMENTS

| | | |
|---|---|---|
| 2006/0079829 A1 | 4/2006 | Fulton et al. |
| 2006/0079888 A1 | 4/2006 | Mulier et al. |
| 2006/0122503 A1 | 6/2006 | Burbank et al. |
| 2006/0134185 A1 | 6/2006 | Odermatt et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0241411 A1 | 10/2006 | Field et al. |
| 2006/0292690 A1 | 12/2006 | Liu et al. |
| 2007/0021642 A1 | 1/2007 | Lamoureux et al. |
| 2007/0038145 A1 | 2/2007 | Field |
| 2007/0057794 A1 | 3/2007 | Gisselberg et al. |
| 2007/0083132 A1 | 4/2007 | Sharrow |
| 2007/0087026 A1 | 4/2007 | Field |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0276492 A1 | 11/2007 | Andrews et al. |
| 2007/0287933 A1 | 12/2007 | Phan et al. |
| 2008/0039819 A1 | 2/2008 | Jones et al. |
| 2008/0058640 A1 | 3/2008 | Jones et al. |
| 2008/0091120 A1 | 4/2008 | Fisher |
| 2008/0097199 A1 | 4/2008 | Mullen |
| 2008/0121242 A1 | 5/2008 | Revie et al. |
| 2008/0188768 A1 | 8/2008 | Zarins et al. |
| 2008/0249436 A1 | 10/2008 | Darr |
| 2008/0269638 A1 | 10/2008 | Cooke et al. |
| 2008/0294039 A1 | 11/2008 | Jones et al. |
| 2009/0000629 A1 | 1/2009 | Hornscheidt et al. |
| 2009/0024225 A1 | 1/2009 | Stubbs |
| 2009/0030309 A1 | 1/2009 | Jones et al. |
| 2009/0069713 A1 | 3/2009 | Adams et al. |
| 2009/0076484 A1 | 3/2009 | Fukaya |
| 2009/0093714 A1 | 4/2009 | Chesbrough |
| 2009/0131825 A1 | 5/2009 | Burbank et al. |
| 2009/0171198 A1 | 7/2009 | Jones et al. |
| 2009/0216118 A1 | 8/2009 | Jones et al. |
| 2009/0287078 A1 | 11/2009 | Burbank et al. |
| 2010/0010341 A1 | 1/2010 | Talpade et al. |
| 2010/0010342 A1 | 1/2010 | Burbank et al. |
| 2010/0030072 A1 | 2/2010 | Casanova et al. |
| 2010/0030149 A1 | 2/2010 | Carr, Jr. |
| 2010/0042041 A1 | 2/2010 | Tune et al. |
| 2010/0082102 A1 | 4/2010 | Govil et al. |
| 2010/0121445 A1 | 5/2010 | Corbitt, Jr. |
| 2010/0198059 A1 | 8/2010 | Burbank et al. |
| 2010/0204570 A1 | 8/2010 | Lubock |
| 2010/0298696 A1 | 11/2010 | Field et al. |
| 2010/0298698 A1 | 11/2010 | Burbank et al. |
| 2010/0331668 A1 | 12/2010 | Ranpura |
| 2011/0028836 A1 | 2/2011 | Ranpura |
| 2011/0082547 A1 | 4/2011 | Corbitt, Jr. |
| 2011/0092815 A1 | 4/2011 | Burbank et al. |
| 2011/0184280 A1 | 7/2011 | Jones et al. |
| 2011/0184449 A1 | 7/2011 | Lubock et al. |
| 2012/0078086 A1 | 3/2012 | Hoffa |
| 2012/0078087 A1 | 3/2012 | Curry |
| 2012/0078092 A1 | 3/2012 | Jones et al. |
| 2012/0116215 A1 | 5/2012 | Jones et al. |
| 2012/0179251 A1 | 7/2012 | Corbitt, Jr. |
| 2012/0215230 A1 | 8/2012 | Lubock et al. |
| 2012/0277859 A1 | 11/2012 | Govil et al. |
| 2013/0184562 A1 | 7/2013 | Talpade et al. |
| 2013/0190616 A1 | 7/2013 | Casanova et al. |
| 2013/0253315 A1 | 9/2013 | Burbank et al. |
| 2013/0281847 A1 | 10/2013 | Jones et al. |
| 2013/0310686 A1 | 11/2013 | Jones et al. |
| 2014/0058258 A1 | 2/2014 | Chesbrough et al. |
| 2014/0094698 A1 | 4/2014 | Burbank et al. |
| 2014/0114186 A1 | 4/2014 | Burbank et al. |
| 2014/0142696 A1 | 5/2014 | Corbitt, Jr. |
| 2014/0194892 A1 | 7/2014 | Ranpura et al. |
| 2014/0239528 A1 | 8/2014 | Govil et al. |
| 2014/0243675 A1 | 8/2014 | Burbank et al. |
| 2015/0051477 A1 | 2/2015 | Jones et al. |
| 2015/0164610 A1 | 6/2015 | Field et al. |
| 2015/0245883 A1 | 9/2015 | Talpade et al. |
| 2015/0257872 A1 | 9/2015 | Corbitt, Jr. |
| 2016/0015475 A1 | 1/2016 | Jones et al. |
| 2016/0120510 A1 | 5/2016 | Burbank et al. |
| 2016/0128797 A1 | 5/2016 | Burbank et al. |
| 2016/0199150 A1 | 7/2016 | Field et al. |
| 2017/0100203 A1 | 4/2017 | Field et al. |

FOREIGN PATENT DOCUMENTS

| | | |
|---|---|---|
| EP | 1114618 A2 | 7/2001 |
| EP | 1163888 A1 | 12/2001 |
| EP | 1216721 A2 | 6/2002 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| FR | 2853521 A1 | 10/2004 |
| GB | 708148 | 4/1954 |
| JP | 2131757 A | 5/1990 |
| JP | 2006516468 A | 7/2006 |
| JP | 2007537017 A | 12/2007 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 3/1995 |
| WO | 9806346 A1 | 2/1998 |
| WO | 9908607 A1 | 2/1999 |
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0054689 A1 | 9/2000 |
| WO | 0108578 A1 | 2/2001 |
| WO | 0170114 A1 | 9/2001 |
| WO | 0207786 A2 | 1/2002 |
| WO | 0241786 A2 | 5/2002 |
| WO | 03000308 A1 | 1/2003 |
| WO | 2004045444 A2 | 6/2004 |
| WO | 2005013832 A1 | 2/2005 |
| WO | 2005089664 A1 | 9/2005 |
| WO | 2005112787 A2 | 12/2005 |
| WO | 2006012630 A2 | 2/2006 |
| WO | 2006056739 A2 | 6/2006 |
| WO | 2006097331 A2 | 9/2006 |
| WO | 2006105353 A2 | 10/2006 |
| WO | 2007067255 A1 | 6/2007 |
| WO | 2007069105 A2 | 6/2007 |
| WO | 2008073965 A2 | 6/2008 |
| WO | 2008077081 A2 | 6/2008 |

OTHER PUBLICATIONS

H. J. Gent, M.D., et al., Stereotaxic Needle Localization and Cytological Diagnosis of Occult Breast Lesions, Annals of Surgery, Nov. 1986, pp. 580-584, vol. 204—No. 5.

Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.

Jong-Won Rhie, et al. "Implantation of Cultured Preadipocyte Using Chitosan/Alginate Sponge", Key Engineering Materials, Jul. 1, 2007, pp. 346-352, XP008159356, ISSN: 0252-1059, DOI: 10.4028/www.scientific.net/KEM.342-343.349, Department of

(56) References Cited

OTHER PUBLICATIONS

Plastic Surgery, College of Medicine, The Catholic University of Korea, Seoul Korea.
International Search Report for PCT/US2009/000945 dated Jul. 16, 2009.
Written Opinion of the International Searching Authority for PCT/US2009/000945 dated Jul. 16, 2009.
International Search Report for PCT/US2007/016902 dated Feb. 28, 2008.
International Search Report for PCT/US2007/016902 dated Feb. 4, 2009.
Written Opinion of the International Searching Authority for PCT/US2007/016902 dated Feb. 4, 2009.
International Search Report for PCT/US2007016918 dated Nov. 26, 2007.
Written Opinion of the International Searching Authority for PCT/US2007016918 dated Feb. 4, 2009.
Crook, et al. (Prostate Motion During Standard Radiotherapy As Assessed by Fiducial Markers, 1995, Radiotherapy and Oncology 37:35-42.).
Shah, et al. (Polyethylene Glycol as a Binder for Tablets, vol. 66, No. 11, Nov. 1977, Journal of Pharmaceutical Sciences).
Zmora, et al. (Tailoring the pore architecture in 3-D alginate scaffolds by controlling the freezing regime during fabrication, 2001, Elsevier Science Ltd.).
Madihally, et al. (Porous chitosan scaffolds for tissue engineering, 1998, Elsevier Science Ltd.).
Hyeong-Ho, et al. (Preparation of Macroporous Hydroxyapatite/Chitosan-Alginate Composite Scaffolds for Bone Implants, 2007, Trans Tech Publications).
Armstrong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.
Fucci, V., et al., "Large Bowel Transit Times Using Radioopaque Markers in Normal Cats", J. of Am. Animal Hospital Assn., Nov.-Dec. 1995 31 (6) 473-477.
Schindlbeck, N.E., et al., "Measurement of Colon Transit Time", J. of Gastroenterology, No. 28, pp. 399-404, 1990.
Shiga, et al., Preparation of Poly(D, L-lactide) and Copoly(lactide-glycolide) Microspheres of Uniform Size, J. Pharm. Pharmacol. 1996 48:891-895.
Eiselt, P. et al, "Development of Technologies Aiding Large—Tissue Engineering", Biotechnol. Prog., vol. 14, No. 1, pp. 134-140, 1998.
Press release for Biopsys Ethicon Endo-Surgery (Europe) GmbH; The Mammotome Vacuum Biopsy System. From: http://www.medicine-news.com/articles/devices/mammotome.html. 3 pages.
Johnson & Johnson: Breast Biopsy (minimally invasive): Surgical Technique: Steps in the MAMOTOME Surgical Procedure. From http://www.jnjgateway.com. 3 pages.
Johnson & Johnson: New Minimally Invasive Breast Biopsy Device Receives Marketing Clearance in Canada; Aug. 6, 1999. From http://www.jnjgateway.com. 4 pages.
Johnson & Johnson: Mammotome Hand Held Receives FDA Marketing Clearance for Minimally Invasive Breast Biopises; Sep. 1, 1999. From From http://www.jnjgateway.com. 5 pages.
Johnson & Johnson: The Mammotome Breast Biopsy System. From: http://www.breastcareinfo.com/aboutm.htm. 6 pages.
Cook Incorporated: Emoblization and Occlusion. From: www.cookgroup.com 6 pages.
Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.
Dewanjee et al., "Identification of New Collagen Formation with 1251-Labeled Antibody in Bovine Pericardial Tissue Valves Implanted in Calves", Nucl. Med. Biol. vol. 13, No. 4, pp. 413-422, 1986.
Ma, Jianbiao, et al. "A preliminary in vitro study on the fabrication and tissue engineering applications of a novel chitosan bilayer material as a scaffold of human neofetal dermal fibroblasts." 8iomaterials 22.4 (2001 ): 331-336.
Pignolet, Louis H., et al. "The alginate demonstration: Polymers, food science, and ion exchange." J. Chem. Educ 75.11 (1998): 1430.

* cited by examiner

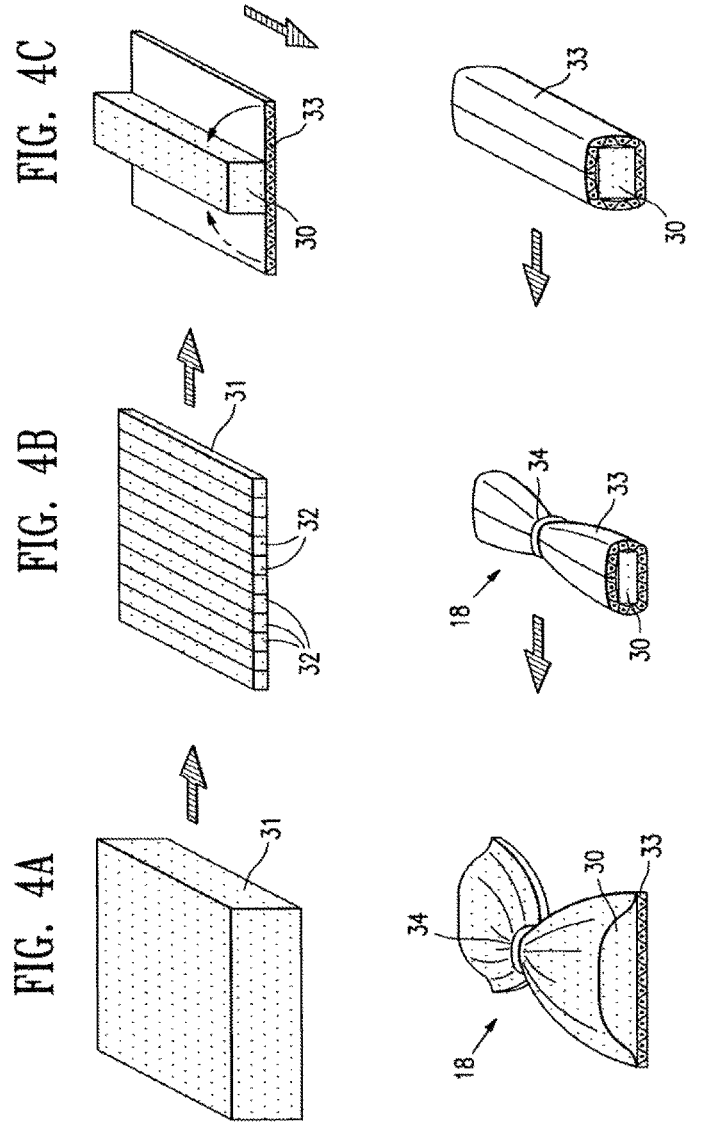

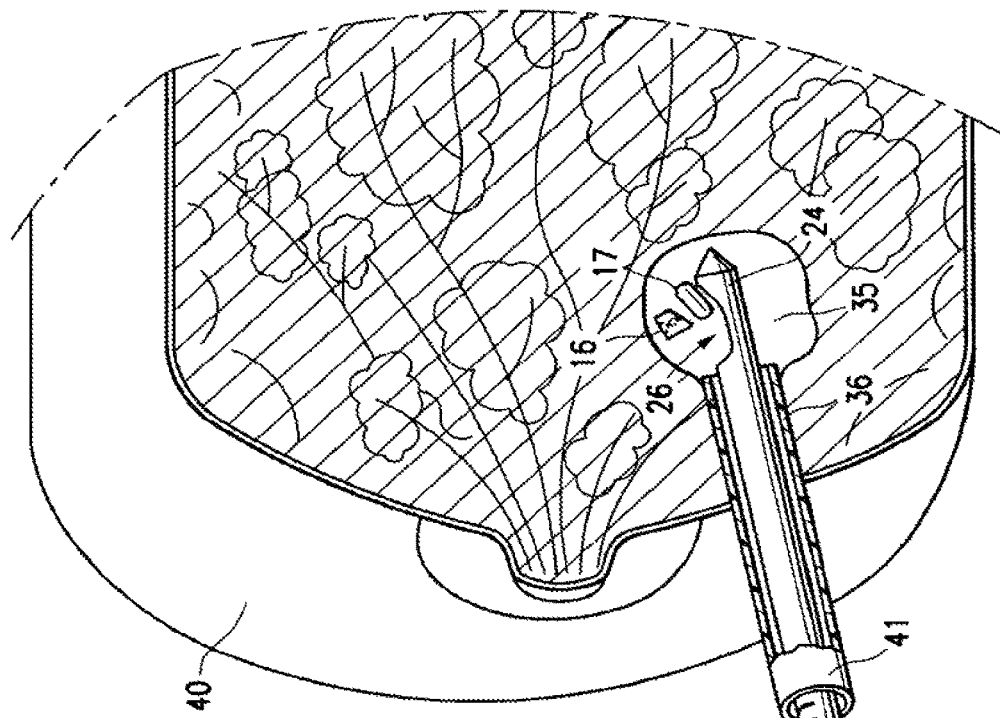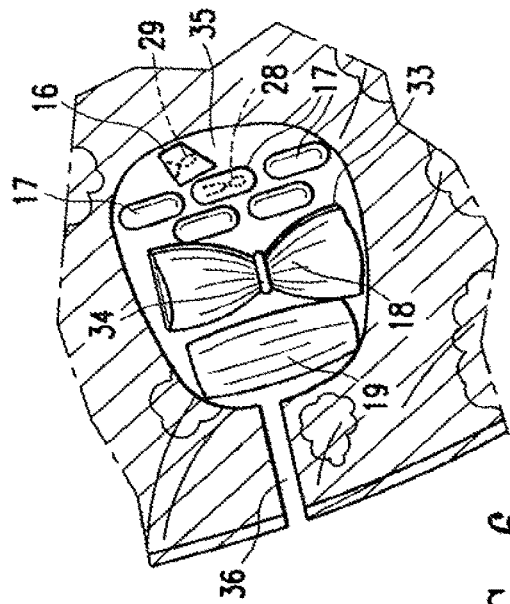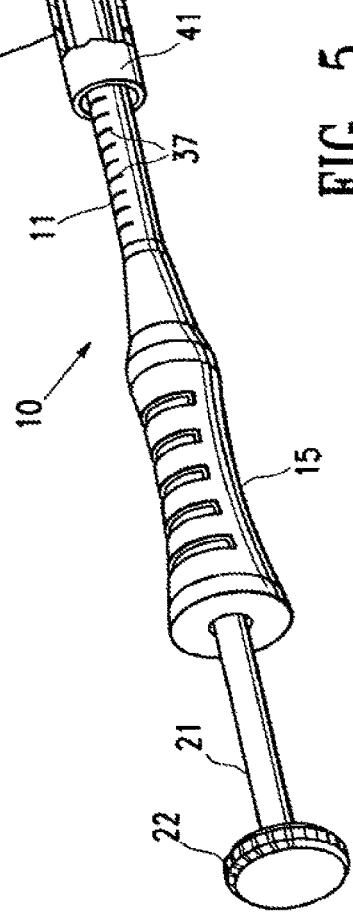

MARKER DELIVERY DEVICE WITH RELEASABLE PLUG

CROSS REFERENCE TO RELATED APPLICATIONS

This application is a continuation of U.S. application Ser. No. 13/750,341, filed Jan. 25, 2013, now U.S. Pat. No. 9,044,162, which is a continuation of U.S. application Ser. No. 13/037,971, filed Mar. 1, 2011, now U.S. Pat. No. 8,361,082, which is a continuation-in-part of U.S. patent application Ser. No. 10/753,694 entitled "MARKER DELIVERY DEVICE WITH RELEASABLE PLUG", filed Jan. 7, 2004, now abandoned, which is a continuation-in-part of U.S. patent application Ser. No. 10/444,770, filed May 23, 2003, now U.S. Pat. No. 7,983,734.

Also, U.S. application Ser. No. 13/037,971, now U.S. Pat. No. 8,361,082, is a continuation-in-part of U.S. patent application Ser. No. 12/852,286 entitled CAVITY-FILLING BIOPSY SITE MARKERS, filed Aug. 6, 2010, now U.S. Pat. No. 8,219,182, which is a continuation of U.S. patent application Ser. No. 10/990,327, filed Nov. 16, 2004, now U.S. Pat. No. 7,792,569, which is a continuation of U.S. patent application Ser. No. 10/124,757, filed Apr. 16, 2002, now U.S. Pat. No. 6,862,470, which is a continuation-in-part of U.S. patent application Ser. No. 09/717,909, filed Nov. 20, 2000, now U.S. Pat. No. 6,725,083, which is a continuation-in-part of U.S. patent application Ser. No. 09/343,975, filed Jun. 30, 1999, now U.S. Pat. No. 6,347,241, which is a continuation-in-part of U.S. patent application Ser. No. 09/241,936, filed Feb. 2, 1999, now U.S. Pat. No. 6,161,034.

Also, U.S. application Ser. No. 13/037,971, now U.S. Pat. No. 8,361,082, is a continuation-in-part of U.S. patent application Ser. No. 12/592,020 entitled PLUGGED TIP DELIVERY TUBE FOR MARKER PLACEMENT, filed Nov. 18, 2009, now U.S. Pat. No. 8,177,792, which is a continuation of U.S. patent application Ser. No. 10/174,401, filed Jun. 17, 2002, now U.S. Pat. No. 7,651,505.

All the above from which priority is claimed and are incorporated herein by reference in their entireties.

BACKGROUND OF THE INVENTION

1. Field of the Invention

The invention is generally directed to devices and methods for the delivery of remotely detectable markers to a desired location within a patient's body. In particular, the invention is directed to devices and methods configured to retain a remotely detectable marker within a delivery device before delivery to a desired intracorporeal location.

2. Description of the Related Art

In diagnosing and treating certain medical conditions, it is often desirable to mark a suspicious body site for the subsequent taking of a biopsy specimen, for delivery of medicine, radiation, or other treatment, for the relocation of a site from which a biopsy specimen was taken, or at which some other procedure was performed. As is known, obtaining a tissue sample by biopsy and the subsequent examination are typically employed in the diagnosis of cancers and other malignant tumors, or to confirm that a suspected lesion or tumor is not malignant. The information obtained from these diagnostic tests and/or examinations is frequently used to devise a therapeutic plan for the appropriate surgical procedure or other course of treatment.

In many instances, the suspicious tissue to be sampled is located in a subcutaneous site, such as inside a human breast. To minimize surgical intrusion into a patient's body, it is often desirable to insert a small instrument, such as a biopsy needle, into the body for extracting the biopsy specimen while imaging the procedure using fluoroscopy, ultrasonic imaging, x-rays, magnetic resonance imaging (MRI) or any other suitable form of imaging technique. Examination of tissue samples taken by biopsy is of particular significance in the diagnosis and treatment of breast cancer. In the ensuing discussion, the biopsy and treatment site described will generally be the human breast, although the invention is suitable for marking biopsy sites in other parts of the human and other mammalian body as well.

Periodic physical examination of the breasts and mammography are important for early detection of potentially cancerous lesions. In mammography, the breast is compressed between two plates while specialized x-ray images are taken. If an abnormal mass in the breast is found by physical examination or mammography, ultrasound may be used to determine whether the mass is a solid tumor or a fluid-filled cyst. Solid masses are usually subjected to some type of tissue biopsy to determine if the mass is cancerous.

If a solid mass or lesion is large enough to be palpable, a tissue specimen can be removed from the mass by a variety of techniques, including but not limited to open surgical biopsy, a technique known as Fine Needle Aspiration Biopsy (FNAB) and instruments characterized as "vacuum assisted large core biopsy devices".

If a solid mass of the breast is small and non-palpable (e.g., the type typically discovered through mammography), a vacuum assisted large core biopsy procedure is usually used. In performing a stereotactic biopsy of a breast, the patient lies on a special biopsy table with her breast compressed between the plates of a mammography apparatus and two separate x-rays or digital video views are taken from two different points of view. A computer calculates the exact position of the lesion as well as depth of the lesion within the breast. Thereafter, a mechanical stereotactic apparatus is programmed with the coordinates and depth information calculated by the computer, and such apparatus is used to precisely advance the biopsy needle into the small lesion. The stereotactic technique may be used to obtain histologic specimens. Usually at least five separate biopsy specimens are obtained from locations around the small lesion as well as one from the center of the lesion.

The available treatment options for cancerous lesions of the breast include various degrees of mastectomy or lumpectomy, radiation therapy, chemotherapy and combinations of these treatments. However, radiographically visible tissue features, originally observed in a mammogram, may be removed, altered or obscured by the biopsy procedure, and may heal or otherwise become altered following the biopsy. In order for the surgeon or radiation oncologist to direct surgical or radiation treatment to the precise location of the breast lesion several days or weeks after the biopsy procedure was performed, it is desirable that a biopsy site marker be placed in the patient's body to serve as a landmark for subsequent location of the lesion site. A biopsy site marker may be a permanent marker (e.g., a metal marker visible under x-ray examination), or a temporary marker (e.g., a bioresorbable marker detectable with ultrasound). While current radiographic type markers may persist at the biopsy site, an additional mammography generally must be performed at the time of follow up treatment or surgery in order to locate the site of the previous surgery or biopsy. In addition, once the site of the previous procedure is located using mammography, the site must usually be marked with a location wire which has a hook on the end which is advanced into site of the previous procedure. The hook is meant to fix the tip of the location wire with respect to the site of the previous procedure so that the patient can then be removed from the confinement of the mammography apparatus and the follow-up procedure performed. However, as the patient is removed from the mammography apparatus, or otherwise transported the position of the location wire can change or shift in relation to the site of the previous procedure. This, in turn, can result in follow-up treatments being misdirected to an undesired portion of the patient's tissue.

As an alternative or adjunct to radiographic imaging, ultrasonic imaging (herein abbreviated as "USI") or visualization techniques can be used to image the tissue of interest at the site of interest during a surgical or biopsy procedure or follow-up procedure. USI is capable of providing precise location and imaging of suspicious tissue, surrounding tissue and biopsy instruments within the patient's body during a procedure. Such imaging facilitates accurate and controllable removal or sampling of the suspicious tissue so as to minimize trauma to surrounding healthy tissue.

For example, during a breast biopsy procedure, the biopsy device is often imaged with USI while the device is being inserted into the patient's breast and activated to remove a sample of suspicious breast tissue. As USI is often used to image tissue during follow-up treatment, it may be desirable to have a marker, similar to the radiographic markers discussed above, which can be placed in a patient's body at the site of a surgical procedure and which are visible using USI. Such a marker enables a follow-up procedure to be performed without the need for traditional radiographic mammography imaging which, as discussed above, can be subject to inaccuracies as a result of shifting of the location wire as well as being tedious and uncomfortable for the patient.

Placement of a marker or multiple markers at a location within a patient's body requires delivery devices capable of holding markers within the device until the device is properly situated within a breast or other body location. Accordingly, devices and methods for retaining markers within a marker delivery device while allowing their expulsion from the devices at desired intracorporeal locations are desired.

SUMMARY OF THE INVENTION

The invention is generally directed to the delivery of one or more markers to an intracorporeal site within a patient's body. A marker delivery device embodying features of the invention include a delivery tube or cannula having an inner lumen leading to a discharge opening and having a releasable plug which is disposed at least in part within the inner lumen and which at least partially occludes the discharge opening in the distal end of the delivery tube.

The releasable plug is configured to occlude or block off the discharge opening of the delivery cannula or the inner lumen leading thereto to prevent tissue and fluid from entering the inner lumen through the discharge opening during delivery and to hold in any other markers within the inner lumen proximal to the releasable plug during handling and delivery. In one embodiment having features of the invention, the delivery device has a releasable plug with a remotely detectable marker element incorporated therein. Preferably, the marker element incorporated into the releasable plug is non-magnetic and remotely detectable by magnetic resonance imaging.

In yet another embodiment having features of the invention, the delivery device has a releasable plug and has at least one short term, remotely detectable marker mass in the inner lumen or at least one fibrous marker in the inner lumen proximal to the releasable plug. Preferably, at least one short term marker and at least one fibrous marker are disposed within the inner lumen of the delivery cannula.

The releasable plug may be secured within the inner lumen by a variety of means, but it is preferred to press fit the plug into the distal portion of the inner lumen so as to occlude the discharge opening. However, the plug may alternatively be mechanically or adhesively secured within the distal portion of the inner lumen. For further plug details see application Ser. No. 10/174,401, filed on Jun. 17, 2002, now U.S. Pat. No. 7,651,505, entitled Plugged Tip Delivery Tube For Marker Placement which is incorporated herein in its entirety by reference. However, the releasable plug should be configured to be easily pushed out of the discharge opening of the delivery cannula, even if the releasable plug has swollen due to contact with a water based fluid. As described above, the releasable plug preferably has a non-magnetic, MRI detectable element which does not interfere with the subsequent imaging of adjacent tissue. The MRI detectable element is about 0.5 to about 5 mm in maximum dimension, preferably about 1 to about 3 mm. Suitable non-magnetic, MRI detectable materials include titanium, platinum, gold, iridium, tantalum, tungsten, silver, rhodium and the like.

The releasable plug is formed of a biocompatible, preferably bioabsorbable material such as oxidized regenerated cellulose, polyethylene glycol, polylactic acid, polyglycolic acid, polycaproic acid, and copolymers, polymer alloys, polymer blends, and combinations thereof. Preferable materials are oxidized regenerated cellulose and polymers of polyethylene glycol with molecular weights of about 5000 to about 120,000 Daltons. The releasable plug should be formed of a water swellable material, so that it swells upon contact with water based fluids (e.g. body fluids) to further occlude or otherwise seal the discharge opening of the delivery cannula and thereby prevent premature contact of body fluids with any markers within the inner lumen proximal to the releasable plug. The plug may also be formed of fibrous materials and be in the form of a fibrous marker described below.

The short term markers disposed within the inner lumen of the delivery cannula proximal to the releasable plug should be remotely detectable for at least two weeks, preferably at least up to six weeks, but not longer than about one year, preferably not more than about six months, so as to not interfere with subsequent imaging of the target site. The short term markers are preferably formed of bioabsorbable polymeric materials such as polymers of lactic acid, glycolic acid and caprolactones and copolymers and blends thereof. Other suitable materials include those described in application Ser. No. 09/717,909, filed Nov. 20, 2000, now U.S. Pat. No. 6,725,803 and application Ser. No. 10/124,757, filed on Jun. 17, 2002, now U.S. Pat. No. 6,862,470, both of which are incorporated by reference in their entireties. The plug and the short term markers may be formed of the same or similar material. The releasable plug may also be formed of fibrous material and be in the form of the fibrous markers described below.

The fibrous marker should be slidably disposed within the inner lumen of the delivery cannula, preferably proximal to at least one short term marker so that upon discharge from the cannula into a target site, the fibrous marker will block the accessing passageway and prevent loss of marker material therethrough. A suitable material for forming the fibrous marker is a felt and/or fiber material formed of oxidized regenerated cellulose which has an in vivo lifetime of a few hours up to about 6 weeks, typically about 3 days to about 4 weeks. However, the fibrous marker may be formed of a bioabsorbable polymer such as polylactic acid or polyglycolic acid, a co-polymer of polylactic acid and polyglycolic acid, polycaprolactone, collagen and mixtures thereof, including mixtures with oxidized regenerated cellulose. Suitable oxidized, regenerated cellulose includes SURGICEL™ from the Ethicon Division of Johnson & Johnson or other suitable oxidized regenerated cellulose which are naturally hemostatic. Alternatively, a hemostatic agent such as collagen, gelatin or polysaccharides may be incorporated into the fibrous material to provide the hemostasis upon contact with blood. A wide variety of other hemostatic agents may be incorporated into the marker. The thrombus formed by the hemostasis is formed very quickly to fill the cavity at the biopsy site and at least temporarily hold the plug and any other markers in position within the cavity. Anesthetic agents to control post procedure pain, chemotherapeutic agents to kill any residual neoplastic tissue and coloring agents (e.g. carbon black and methylene blue) for visual location of the biopsy site, may also be incorporated into the fibrous marker.

The fibrous material is formed into an elongated member, e.g. by rolling or folding, and bound in a compressed condition to provide sufficient column strength to facilitate introduction into and discharge from a tubular delivery device. Suitable binding agents for holding the fibrous marker in a compressed condition are water soluble polymers such as polyvinyl alcohol, polyethylene glycol, polyvinyl pyrollidone. One or more radiographically detectable marker elements are provided with at least one of the fibrous markers, preferably centrally located on the elongated marker to ensure that the radiographically detectable element is disposed at a more or less central location within the target site rather than at a site margin.

The releasable plug, the short term markers and the fibrous markers may include a variety of therapeutic or diagnostic materials such as hemostatic agents, anesthetic agents, coloring agents, antibiotics, antifungal agents, antiviral agents, chemotherapeutic agents, radioactive agents and the like.

The delivery device preferably has a plunger slidably disposed within the inner lumen of the delivery cannula which is movable from an initial position accommodating the releasable plug and any markers proximal to the plug within the tube, to a delivery position to push the plug and any desired number of markers out of the discharge opening in the distal end of the cannula into the target tissue site.

Upon being discharged into the intracorporeal target site, the markers at least partially fill the site to enable short term detection by remote imaging and preferably long term detection by remote imaging without interfering with imaging of tissue adjacent to the site. The markers may swell on contact with body fluid, e.g. blood so as to further fill the biopsy cavity. The fibrous marker partially fills the cavity at the target site, positioning the radiopaque marker element within the interior of the target cavity.

The marker mass proximal to the releasable plug may be in the form of ultrasound-detectable, bio-resorbable finely-divided particulate material (such as a powder or granulated material), in which many of the particles have internal cavities. Such particulate materials preferably have particle sizes less than about 2000 microns, and typically between about 20 microns and about 2000 microns. For optimum delivery and marker resolution, the particulate should have a particulate size of about 20 microns to about 1500 microns, preferably about 500 microns to about 800 microns. The ultrasound-detectable, bio-resorbable particulate materials may be formed of polymeric materials such as polylactic acid, polyglycolic acid, polycaprolactone, and combinations of these polymers and the particulate may be bound by suitable binding agents such as gelatin, polyethylene glycol, polyvinyl alcohol, glycerin, polysaccharides, other hydrophilic materials, and combinations of these. Suitable gelatins include bovine collagen, porcine collagen, ovine collagen, equine collagen, synthetic collagen, agar, synthetic gelatin, and combinations of these. Further details of the particulate marker material and the delivery thereof can be found in application Ser. No. 10/124,757, now U.S. Pat. No. 6,862,470, which has been incorporated by reference herein. Polysaccharide particulate or powder may be included with the other particulate materials as a hemostatic agent.

The delivery tube of the device may be configured to fit within a guide cannula, such as a Mammotome® or SenoCor 360™ biopsy cannula or a coaxial needle guide.

The ultrasound-detectable biopsy site markers of the present invention provide several advantages. A biopsy cavity with marker material having features of the present invention provides a large USI-bright mass, making it much easier, for example, to distinguish the ultrasound signal of the marker from signals arising naturally from within a breast. The marker materials produce bright ultrasound echo signals from one portion of the filled region, which contrasts with the dark ultrasound shadow region immediately behind the bright ultrasound echo region. The strength of the reflected signal, and the contrast with the shadow region, make the marked site readily detectable. Such ready detectability allows, for example, less-experienced physicians to perform the identification by USI and the subsequent surgical resection without the need for an interventional radiologist to identify and mark the biopsy cavity. When a MRI marker element is incorporated into the releasable plug or the short term markers, the target site in which the markers are deployed may be subsequently detected by ultrasound, magnetic resonance and X-ray without interfering with imaging adjacent tissue at a later date.

The invention provides the advantages of securely retaining markers within a marker delivery device, improving accuracy and avoiding errors in placement of markers at desired locations within a patient's body, preventing ingress of tissue into the distal tip of the device when it is advanced through tissue, and guiding the device by use of an imaging device including ultrasound, X-ray and magnetic resonance based devices. These and other advantages of the invention will become more apparent from the following description when taken in conjunction with the accompanying drawings.

The invention, in one form thereof, is directed to a marker delivery device that includes an elongated delivery cannula which has a distal end section, an inner lumen and a discharge opening in the distal end section in communication with the inner lumen. At least one elongated fibrous marker body is slidably disposed within the inner lumen of the elongated delivery cannula. The at least one elongated fibrous marker body includes a plurality of bioabsorbable polymeric strands. The strands are compressed to a compressed configuration and bound together in the compressed configuration with a polymer binding agent prior to insertion into the elongated delivery cannula. A releasable plug is disposed within a distal portion of the inner lumen and distal to the at least one elongated fibrous marker body so as to at least partially occlude the discharge opening in the distal end section.

The invention, in another form thereof, is directed to a marker delivery device for an intracorporeal tissue site. The marker delivery device includes an elongated delivery cannula which has a distal end section, a discharge opening in the distal end section and an inner lumen extending to and in communication with the discharge opening. A releasable plug has an MRI detectable marker element incorporated therein and is disposed at least in part within a distal portion of the inner lumen so as to partially occlude the discharge opening in the distal end section. A plurality of elongated fibrous marker bodies is slidably disposed within the inner lumen of the elongated delivery cannula proximal to the releasable plug. Each of the plurality of elongated fibrous marker bodies has a length comprising a plurality of separate bioabsorbable fibers which are compressed and bound together with a synthetic polymer binding agent so as to form the length prior to insertion into the elongated delivery cannula. A plunger is slidably disposed within the inner lumen of the elongated delivery cannula with a pusher end proximal to the plurality of elongated fibrous marker bodies in the inner lumen.

The invention in another form thereof is directed to a marker delivery device for an intracorporeal site within a patient. The marker device includes an elongated delivery cannula which has a distal end, a discharge opening in the distal end and an inner lumen extending to and in communication with the discharge opening. A releasable plug is disposed within the inner lumen which partially occludes the discharge opening. At least one short term marker is disposed within the inner lumen proximal to the releasable plug. A plurality of elongated fibrous markers are inserted into and slidably disposed within the inner lumen proximal to the at least one short term marker. Each of the fibrous markers has a length comprising a plurality of separate bioabsorbable fibers that are compressed and bound together with a polymer binding agent prior to insertion into the inner lumen of the elongated delivery cannula.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 4A-4F illustrates forming a fibrous marker with a core member as depicted in FIG. 4.

FIG. 5 is a partially cut away, perspective view of a human breast from which a biopsy specimen has been removed, showing a markers being delivered to the biopsy site with the marker delivery assembly shown in FIG. 1A.

FIG. 6 is a partial cut-away view of a human breast shown in FIG. 2 with the markers delivered into the biopsy site and the delivery device removed.

Corresponding reference characters indicate corresponding parts throughout the several views. The exemplifications set out herein at least one embodiment of the invention, and such exemplifications are not to be construed as limiting the scope of the invention in any manner.

DETAILED DESCRIPTION OF THE INVENTION

Figure 1A:
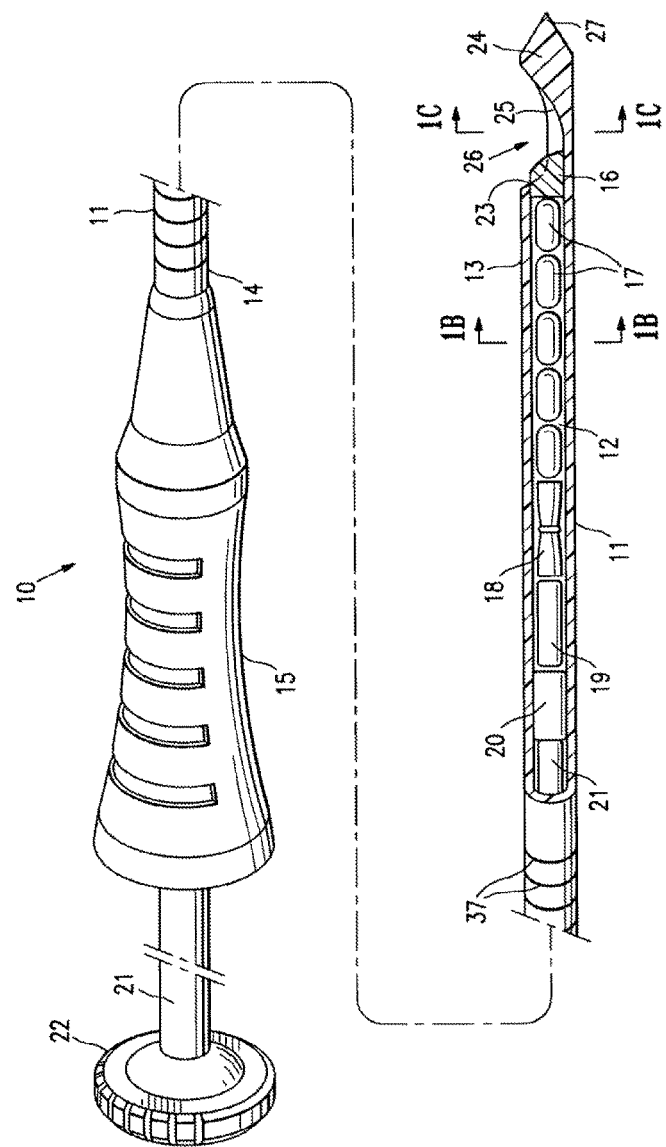
FIG. 1A is a partly cut-away perspective view of a marker delivery assembly embodying features of the invention.
Figure 1B:
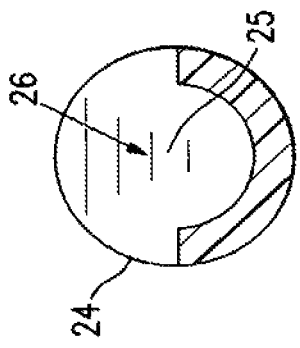
FIG. 1B is a transverse cross-sectional view of the marker delivery assembly of FIG. 1A taken at line 1B-1B.
Figure 1C:
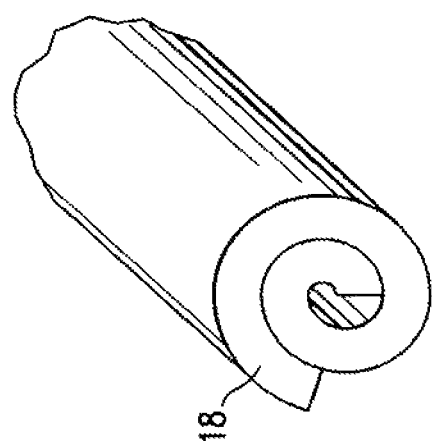
FIG. 1C is a transverse cross-sectional view of the marker delivery assembly of FIG. 1A taken at line 1C-1C.

FIGS. 1A-1C illustrate a marker delivery device 10 embodying features of the invention which includes a delivery tube or cannula 11 with a bore 12, a distal portion 13, and a proximal portion 14 with a handle 15. A releasable distal plug 16, several (five) short term markers 17, a pair of fibrous markers 18 and 19 and a proximal plug 20 are shown disposed within the bore 12. A plunger 21 is slidably disposed within the tube bore 12, and is provided with a proximal end 22 configured to allow an operator to press the plunger further into the bore 12 and push the releasable plug 16 and one or more of the other markers out of the discharge port or opening 23 in the distal end 24 of delivery tube 11. Cannula handle 15 allows an operator to hold the cannula steady while pressing plunger 21 to discharge the releasable plug 16 and markers 17 and 18.

Releasable plug 16 may substantially fill the discharge opening 23, as shown in FIG. 1, or may occupy or block only a portion of the discharge opening 23. The exposed face of plug 16 is preferably provided with an inclined configuration to conform with the inclination of the discharge opening 23.

Markers 17, 18 and 19 and proximal plug 20 are preferably configured to slide readily within tube bore 12. Releasable plug 16 is configured to be tight enough, e.g. press fit, in the bore 12 to prevent its inadvertent release which would allow premature discharge of markers 17, 18 and 19 from delivery tube 11 and undesirable contact with body fluid. But the plug 16 must be easily released when the plunger 21 is pressed deeper into the bore 12 of the delivery tube 11. An adhesive or mechanical element(s) may be used to hold the releasable plug 16 in a position within the bore 12 to occlude the discharge opening 23. Suitable adhesives include polyurethane or polyacrylic based adhesives, polyhydroxymethacrylate base adhesives, fibrin glue (e.g., Tisseal™), collagen adhesive, or mixtures thereof. Suitable mechanical means for securing the releasable plug 16 are described in application Ser. No. 10/174,401, now U.S. Pat. No. 7,651,505, which has been incorporated herein. The distal end 24 of the delivery cannula 11 is provided with a ramp 25 which guides the discharged plug 16 and markers 17, 18 and 19 out of the side port 26 into the target site. The distal tip 27 may be tapered for delivery through a guide tube as shown.

The delivery tube 11 may be provided with markings 28 which serve as visual landmarks to aid an operator in accurately placing the distal end 24 of the cannula 11 in a desired location within a patient's body for discharging the markers. The markings 37 also be radiopaque, ultrasound-reflective, or otherwise configured to be detectable by remote imaging devices and imaging methods.

Short term markers 17 are made at least in part with detectable, biocompatible materials. Suitable marker materials include bioresorbable polymeric materials such as poly(esters), poly(hydroxy acids), poly(lactones), poly (amides), poly(ester-amides), poly(amino acids), poly(anhydrides), poly(ortho-esters), poly(carbonates), poly(phosphazines), poly(thioesters), poly(urethanes), poly(ester urethanes), polysaccharides, polylactic acid, polyglycolic acid, polycaproic acid, polybutyric acid, polyvaleric acid, and copolymers, polymer alloys, polymer blends, and combinations thereof. Preferable polymeric materials are polymers of lactic acid, glycolic acid and caprolactones. The short term markers 17 may also be formed at least in part of gelatin. One or more of the short term markers 17 may include a remotely detectable preferably radiopaque element 28.

Releasable plug 16 is preferably formed at least in part of oxidized regenerated cellulose or polyethylene glycol, but may be made from the same or similar bioabsorbable materials as marker 17. The polyethylene glycol quickly expands when contacting a water based fluid such as blood, which ensures that the releasable plug seals off the discharge opening to prevent premature contact between body fluid (or other water based fluid) and the markers 17, 18 and 19 within the bore 12. The polyethylene glycol should have a molecular weight of about 5000 to about 20000 Daltons, preferably about 8000 to about 10000 Daltons in the final plug form. The releasable plug 16 preferably has a non-magnetic element 29 incorporated within the body of the releasable plug that is remotely detectable by magnetic resonance imaging (MRI). It may be formed of titanium, platinum, gold, iridium, tantalum, tungsten, silver, rhodium and the like. The MRI detectable element 29 should have a maximum dimension of about 0.5 to about 5 mm, preferably about 1 to about 3 mm to be MRI detectable. Elements with dimensions greater than about 5 mm tend to interfere with the imaging of adjacent tissue.

Releasable plug 16, markers 17, 18 and 19, and plug 20 are configured for a slidable fit within the bore 12 of the delivery tube 11. The exterior of the delivery tube 11 is preferably configured to fit within a guide cannula sized to accept a Mammotome®, Tru-Cut®, or SenoCor® biopsy device. Typically, plug 16 and markers 17 and 18 will have diameters determined by the size of the bore 12 and typically will be about 0.02 inch (0.5 mm) to about 0.5 inch (12 mm), preferably about 0.04 inch (1 mm) to about 0.3 inch (8 mm). Plug 16 may have slightly larger transverse dimensions to provide a tight fit. In addition, plugs 16 and 20 and short term markers 17 will have a length of about 0.04 inch (1 mm) to about 0.8 inch (20 mm), preferably about 0.1 inch (2.5 mm) to about 0.6 inch (15 mm).

Figure 2:
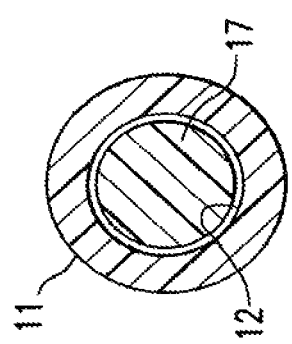
FIG. 2 is an end perspective view of a fibrous marker with a core member suitable for use with a marker delivery system embodying features of the invention.
Figure 3:
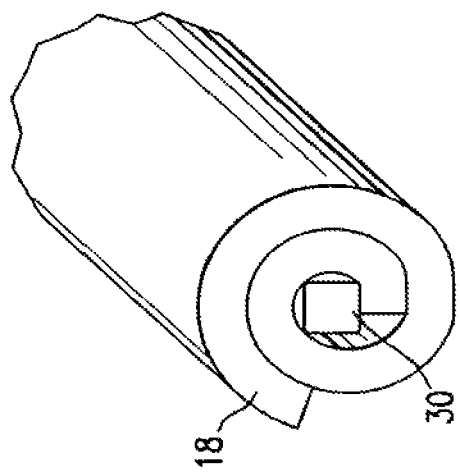
FIG. 3 is an end perspective view of an alternative fibrous marker without a core member suitable for use with a marker delivery system embodying features of the invention.

The fibrous markers 18 and 19 are preferably rolled or folded pieces of fibrous material such as oxidized cellulose or oxidized, regenerated cellulose which has been compressed and impregnated with a binding agent such as polyethylene glycol and freeze dried in the compressed condition. The fibrous material may be rolled up by itself, as shown in FIG. 3, or wrapped about a matt-like core 30 as shown in FIG. 2. The fibrous marker is generally configured to be slidably disposed within the inner lumen of the delivery cannula 11, and before delivery is about 0.5 mm to about 12 mm, preferably about 1 to about 8 mm in diameter and about 5 to about 30 mm, preferably about 10 to about 25 mm in length. Upon contact with a body fluid or other water based fluid, the length of the fibrous marker remains about the same but the wrapped structure unfolds upon swelling to a width of about 5 to about 25 mm, usually about 10 to about 20 mm. With a radiopaque marker element clamped about a center portion of the wrapped fibrous marker, the fibrous marker expands into a generally bow-tie shape when exposed to body fluids. However, even though secured to the fibrous marker, the radiopaque marker element need not restrict the expansion of the fibrous marker.

The manufacture and use of fibrous marker 18 with a core 30 is schematically illustrated in FIGS. 4A-4F. A felt pad or mat 31 of oxidized, regenerated cellulose about 0.125 to about 0.375 inch (3.2-9.3 mm), preferably about 0.25 inch (6.4 mm) thick is impregnated with a 10% (Wt.) polyethylene glycol in a 70% isopropyl alcohol solution and then compressed to a mat about 0.03 to about 0.05 inch (0.76-1.3 mm) thick. A reduction in thickness of 80% or more is suitable. The compressed mat 31 is cut up into elongated strips 32 with square or near square transverse cross-sectional shapes which form the core 30. The core 30 is wrapped in a fabric 33 (i.e., jacket) of oxidized regenerated cellulose about 5 to about 10 mm in width and about 20 mm in length, compressed and impregnated with the 10% PEG dispersion and then freeze dried to a diameter of about 0.065 inch (1.65 mm). Elevated temperatures may be employed to dry the material. The fabric 33 should make at least one, preferably two or more complete wraps about the core 30. The wrapped and compressed product may then be cut to a desired length to form the fibrous marker 18. Alternatively, the uncompressed mat 31, the strip 32 and fiber wrap 33 may be provided at the desired length for the fibrous marker 18, wrapped and then compressed. A radiographically detectable marker element 34 may be formed of a radiopaque wire about 0.005 to about 0.01 inch, (0.13-0.25 mm) may then be crimped about or embedded in a central portion (or other desired portion) of the marker 18. The fibrous marker 18 is then ready for deployment. As shown in FIG. 1A, only fibrous marker 18 is provided with marker element 34. Marker 19 may be formed in the same or similar manner but without the radiopaque element 34.

Fibrous markers without the core member 30 may be formed by rolling or folding into the desired configuration. The fibrous material, oxidized rayon felt is first impregnated with a 10% PEG dispersion, compressed and then freeze dried. The dried felt material is rolled again compressed in the rolled state, impregnated with a 10-30% PEG solution, and freeze dried in the rolled compressed condition. The rayon felt material can be initially oxidized by treating in a solution of 80% (by vol.) Nitric Acid, 20% (by vol.) Sulfuric Acid and 1% (by weight) Sodium Nitrite. The felt is treated in the oxidizing, acidic solution at room temperature for about 4.5 hours and then rinsed with deionized water.

Radiopaque elements 28 and 34 may be made with suitable radiopaque material, including stainless steel, platinum, gold, iridium, titanium, tantalum, tungsten, silver, rhodium, nickel, bismuth, other radiopaque metals, alloys and oxides of these metals, barium salts, iodine salts, iodinated materials, and combinations of these. The radiopaque elements 28 and 34 may also be configured for detection by MRI. Radiopaque materials and markers may be permanent, or may be temporary and not detectable after a period of time subsequent to their placement within a patient. Colorants, such as dyes (e.g., methylene blue and carbon black) and pigments (e.g., barium sulfate), may also be included in markers 17 and 19 and plugs 16 and 20 embodying features of the invention.

FIG. 5 schematically illustrates the use of a marker delivery system 10 to deliver markers to a desired location 35 within a patient's body. The desired location 35 is typically a cavity from which a biopsy sample has been, or is to be, taken, or a lesion that has been or will be removed or otherwise treated. In FIG. 5, the marker delivery system 10 is shown inserted into a breast 40 through a guide cannula 41 until the distal end 24 is disposed at the delivery site, cavity 35 where a tissue specimen has been removed. While an operator holds the system 10 by the handle 15 of the delivery tube 11, the plunger 21 is pressed further into the bore 12 of delivery cannula 11 to discharge the releasable plug 16 and markers 17, 18 and 19 into the cavity 35. FIG. 6 schematically illustrates the plug 16 and markers 17, 18 and 19 within the cavity 35 after deployment. When the markers contact body fluid within the cavity 35, they tend to swell and thereby further fill the cavity. The fibrous markers 18 and 19 generally block the accessing track 36 to the cavity 35 so that none of the smaller markers 17 will be lost through the track 36. Marks 37 are provided on the proximal end of cannula 11 to provide end location information to the operator.

Figure 7:
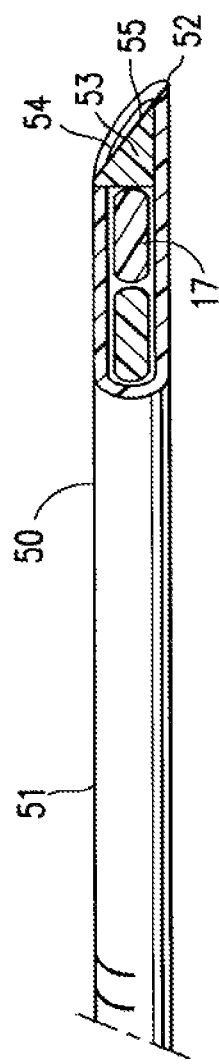
FIG. 7 is a longitudinal cross-sectional view of the distal portion of an alternative marker delivery device embodying features of the invention with a sharp, tissue penetrating distal tip.

FIG. 7 illustrates the distal portion 50 of cannula 51 of an alternative delivery system that is essentially the same as that shown in FIGS. 1A-1C except that the distal tip 52 of cannula 51 is configured in a needle-like shape. The delivery system cannula 51 may be used in conjunction with a guide cannula (not shown) or the cannula 51 can be inserted directly through tissue to reach the target site without the need for a guide cannula. The releasable plug 53 is secured in the discharge opening 54 as in the previously discussed embodiment. The exposed face 55 of the plug 53 is preferably flush with the discharge opening 54 of the distal tip 52.

Insertion of marker delivery devices embodying features of the invention may be performed with or without the aid of an imaging device, such as an ultrasound imaging device, an X-ray imaging device, a MRI device, or other imaging device. Alternatively, or additionally, insertion may be visually guided, or may be guided by palpation or by other means.

The size and composition of the short term markers 17 are selected so as to remain in place within the patient and be detectable by ultrasound for at least 2 weeks, preferably at least 6 weeks to have practical clinical value. However, the short term markers should not be detectable by ultrasound after about one year, preferably not after about six months, so as to avoid interfering with subsequent site examination. For most clinical purposes, a suitable in-situ lifespan when the short term marker is ultrasonically detectable is about six to about twenty weeks. The radiopaque and MRI detectable marker elements generally will have much longer lifespans.

Figure 8:
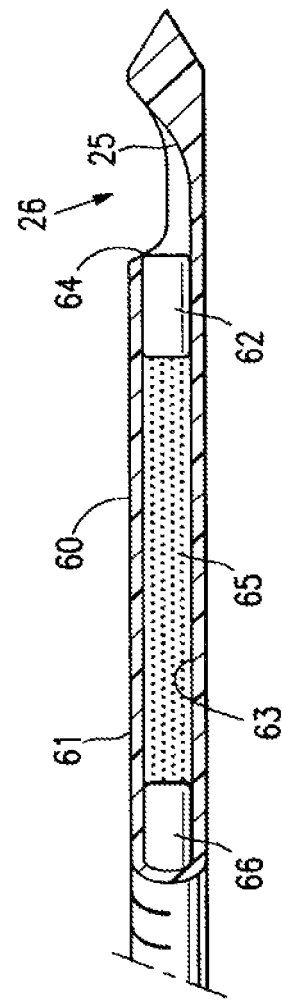
FIG. 8 is a longitudinal cross-sectional view of the distal portion of a marker delivery device embodying features of the invention having particulate marker mass proximal to the releasable plug.

FIG. 8 illustrates the distal shaft section 60 of an alternative delivery cannula 61 which has a fibrous releasable plug 62 in the inner lumen 63 of the distal shaft section which at least partially occludes the discharge opening 64 in the distal end of the shaft. The fibrous releasable plug 62 may be formed as shown in FIGS. 2, 3 and 4A-F.

The inner lumen proximal to the fibrous releasable plug 62 is filled with a particulate marker material 65. The corresponding parts of the system are the same as that shown in FIGS. 1A-1C. Plunger 66 is slidably disposed within the inner lumen 63 to eject the powdered mass 65. The particulate marker material 65 may be discharged dry or mixed with a suitable fluid and discharged as a slurry.

The particulate may be formed of a biocompatible and bio-resorbable polymeric material such as polylactic acid, polyglycolic acid, polycaprolactones, poly(esters), poly(hydroxy acids), poly(lactones), poly(amides), poly(ester-amides), poly(amino acids), poly(anhydrides), poly(orthoesters), poly(carbonates), poly(phosphazines), poly(thioesters), poly(urethanes), poly(ester urethanes), polysaccharides, polybutyric acid, polyvaleric acid, and copolymers, polymer alloys, polymer mixtures, and combinations thereof. Of those, polylactic acid, polyglycolic acid, and polycaproic acid are preferred. The polymeric material in particulate form should have cavities or entrap bubbles which facilitate remote detection.

Suitable particulate materials have particle sizes typically about 20 microns to about 2000 microns, preferably about 20 microns to about 800 microns and more preferably about 300 microns to about 500 microns. The particulate should have cavities for USI with maximum dimensions of about 10 microns to about 500 microns, preferably about 20 microns to about 200 microns. The polymeric particulate materials suitable for use in making ultrasound-detectable biopsy marker materials typically have a bulk density of about 0.8 g/ml to about 1.5 g/ml, preferably about 0.8 g/ml to about 1 g/ml. The particulate may also contain or be mixed with binding agents such as polyethylene glycol, polyvinyl alcohol and the like. Polysaccharide particulate or powder may be incorporated into the particulate mass in amounts up to about 50% (by weight) of the total particulate mass for purposes of hemostasis.

While particular forms of the invention have been illustrated and described herein in the context of a breast biopsy site, it will be apparent that the device and methods having features of the invention may find use in a variety of locations and in a variety of applications, in addition to the human breast. Moreover, various modifications can be made without departing from the spirit and scope of the invention. Accordingly, it is not intended that the invention be limited to the specific embodiments illustrated. It is therefore intended that this invention to be defined by the scope of the appended claims as broadly as the prior art will permit, and in view of the specification if need be. Moreover, those skilled in the art will recognize that features shown in one embodiment may be utilized in other embodiments. Terms such as "element", "member", "device", "section", "portion", "step", "means" and words of similar import when used in the following claims shall not be construed as invoking the provisions of 35 U.S.C. §112(6) unless the following claims expressly use the terms "means" followed by a particular function without specific structure or "step" followed by a particular function without specific action. All patents and patent applications referred to above are hereby incorporated by reference in their entirety.

This application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A marker delivery device for use in marking an intracorporeal tissue site, comprising:
    an elongated delivery cannula which has a distal end section, an inner lumen, and a discharge opening in the distal end section in communication with the inner lumen;
    a plunger slidably disposed within the inner lumen of the elongated delivery cannula, the plunger having a distal end;
    at least one elongated fibrous marker body having a plurality of layers of fibrous material that is pre-formed prior to being inserted into the inner lumen of the elongated delivery cannula, the at least one elongated fibrous marker body being slidably disposed within the inner lumen of the elongated delivery cannula at a location distal to the distal end of the plunger, the pre-formed at least one elongated fibrous marker body being compressed and impregnated with a binding agent and freeze dried in the compressed condition; and a releasable plug disposed within a distal portion of the inner lumen and distal to the at least one elongated fibrous marker body.

2. The marker delivery device of claim 1, wherein the at least one elongated fibrous marker body comprises a plurality of bioabsorbable polymeric strands.

3. The marker delivery device of claim 1, wherein the fibrous material is oxidized cellulose.

4. The marker delivery device of claim 1, wherein the fibrous material is oxidized regenerated cellulose.

5. The marker delivery device of claim 1, wherein the at least one elongated fibrous marker body is formed from:
   a mixture of oxidized regenerated cellulose and a polymer selected from a group consisting of polylactic acid, polyglycolic acid, a co-polymer of polylactic acid and polyglycolic acid, polycaprolactone, and collagen; and
   the binding agent, wherein the binding agent is selected from the group consisting of polyvinyl alcohol, polyethylene glycol and polyvinyl pyrollidone.

6. The marker delivery device of claim 1, wherein the binding agent is selected from a group consisting of polyvinyl alcohol, polyethylene glycol and polyvinyl pyrollidone.

7. The marker delivery device of claim 1, comprising an MRI detectable marker element attached to the at least one elongated fibrous marker body.

8. The marker delivery device of claim 1, wherein the elongated delivery cannula has a plurality of markings regularly spaced along the elongated delivery cannula.

9. The marker delivery device of claim 1, wherein the discharge opening is a lateral discharge opening on the elongated delivery cannula.

10. The marker delivery device of claim 1, wherein each of the plurality of layers is formed of the same fibrous material.

11. A marker delivery device for use in marking an intracorporeal tissue site, comprising:
   an elongated delivery cannula having a distal end section, a discharge opening in the distal end section, and an inner lumen extending to and in communication with the discharge opening;
   a plurality of elongated fibrous marker bodies slidably disposed within the inner lumen of the elongated delivery cannula proximal to the discharge opening, each of the plurality of elongated fibrous marker bodies having a length and comprising a plurality of bioabsorbable fibers which are configured into a plurality of layers, compressed, and bound together with a synthetic polymer binding agent so as to form the length prior to insertion of the plurality of elongated fibrous marker bodies into the elongated delivery cannula; and
   a plunger slidably disposed within the inner lumen of the elongated delivery cannula, the plunger having a pusher end located proximal to the plurality of elongated fibrous marker bodies in the inner lumen.

12. The marker delivery device of claim 11, wherein each of the plurality of elongated fibrous marker bodies is expandable upon contact with body fluid or other water based fluid.

13. The marker delivery device of claim 11, comprising an MRI detectable marker element attached to at least one of the plurality of elongated fibrous marker bodies.

14. The marker delivery device of claim 11, wherein the elongated delivery cannula has a plurality of markings regularly spaced along the elongated delivery cannula.

15. The marker delivery device of claim 11, wherein each of the plurality of layers is formed of the same bioabsorbable fibers.

16. A marker delivery device for use in marking an intracorporeal site within a patient, comprising:
   an elongated delivery cannula which has a distal end, a discharge opening in the distal end, and an inner lumen extending to and in communication with the discharge opening;
   a plunger slidably disposed within the inner lumen of the elongated delivery cannula, the plunger having a pusher end;
   at least one short term marker body disposed within the inner lumen proximal to the discharge opening of the elongated delivery cannula and distal to the pusher end of the plunger, the at least one short term marker body configured for remote detection for at least two weeks but not longer than one year; and
   an elongated fibrous marker body pre-formed prior to being inserted into the inner lumen of the elongated delivery cannula, the elongated fibrous marker body being slidably disposed within the inner lumen proximal to the at least one short term marker and distal to the pusher end of the plunger, the elongated fibrous marker body comprising a plurality of layers of compressed bioabsorbable fibers bound in a compressed condition by a polymer binding agent.

17. The marker delivery device of claim 16, wherein the elongated fibrous marker body is formed from oxidized cellulose.

18. The marker delivery device of claim 16, wherein the elongated fibrous marker body is formed from oxidized regenerated cellulose.

19. The marker delivery device of claim 16, wherein the elongated fibrous marker body is formed from a mixture of oxidized regenerated cellulose and a polymer selected from a group consisting of polylactic acid, polyglycolic acid, a co-polymer of polylactic acid and polyglycolic acid, polycaprolactone, and collagen.

20. The marker delivery device of claim 16, wherein the polymer binding agent is selected from a group consisting of polyvinyl alcohol, polyethylene glycol and polyvinyl pyrollidone.

* * * * *